US006436701B1

(12) United States Patent
Evans et al.

(10) Patent No.: US 6,436,701 B1
(45) Date of Patent: Aug. 20, 2002

(54) DERIVATION OF PLURIPOTENTIAL EMBRYONIC CELL LINES FROM UNGULATE SPECIES

(75) Inventors: Martin John Evans, Cambridge; Robert Michael Moor, Babraham; Elena Notaranni, Cambridge, all of (GB)

(73) Assignee: Babraham Institute, Cambridge (GB)

( * ) Notice: Subject to any disclaimer, the term of this patent is extended or adjusted under 35 U.S.C. 154(b) by 0 days.

(21) Appl. No.: 07/669,403

(22) PCT Filed: Sep. 21, 1989

(86) PCT No.: PCT/GB89/01103

§ 371 (c)(1),
(2), (4) Date: Apr. 23, 1991

(87) PCT Pub. No.: WO90/03432

PCT Pub. Date: Apr. 5, 1990

(30) Foreign Application Priority Data

Sep. 21, 1988 (GB) ............................................. 8822158
Aug. 9, 1989 (GB) ............................................. 8918203

(51) Int. Cl.$^7$ .............................. C12N 5/00; C12N 5/02
(52) U.S. Cl. ....................... 435/325; 435/383; 435/391; 435/392
(58) Field of Search .......................... 435/240.1, 240.2, 435/240.21, 70.3, 325, 383, 391, 392

(56) References Cited

FOREIGN PATENT DOCUMENTS

| EP | 0 169 672 | 1/1986 |
| GB | 2 213 831 A | 8/1989 |

OTHER PUBLICATIONS

Kuehn, et al., "A potential animal model for Lesch—Nyhan syndrome through introduction of HPRT mutations into mice", Nature, vol. 326, No. 6110, pp. 295–298 (1987).
Robertson, et al., "Germ–line transmission of genes introduced into cultured pluripotential cells by retoviral vector", Nature, Co. 323, pp. 445–448 (1986).
Flake, et al., "Transplantation of Fetal Hematopoiatic Stem Cells in Utero: The Creation of of Hematopoletic Chimeras", Science, vol. 233, pp. 776–778.
R.B. Church, "Embryo manipulation and gene transfer in domestic animals", TibTech, vol. 5, pp. 13–19 (1987).
Kohn, et al., "Retroviral–Mediated gene transfer Into Mannalian Cells", Blood Cells, vol. 13, pp. 295–298 (1987).
Gossler, et al., "Transgenesis by means of blastocyst–derived embryonic stem cell lines", Proc. Natl. Acad. Sci.; vol. 83, pp. 9065–9069 (1986).
C.B. Ware, et al., "Development of Embryonic Stem cell lines from farm animals", 21st Annual Meeting of the Society for the Study of Reproduction, Seattle Washington, 38 (Suppl. 1) (1988).
G.G. Magrene, "A comparative Study of Human & Mouse Teratogarcinomas", Thesis.

Palmiter, et al., "Germ–line transformation of mice", Ann. Rev. Genet, vol. 20, pp. 465–499 (1986).
Hooper, et al., "HPRT–deficient (Lesch–Nyhan) mouse embryos derived from germline colonization by cultured cells", Nature, vol. 326, pp. 293–295 (1987).
Van Der Putten, et al., "Efficient insertion of genes into the mouse germ line via retroviral vectors", Proc. Natl. Acad. Sci. vol. 82, pp. 6146–6152 (1985).
Williams, et al., "Introduction of new genetic material into pluripotent haematopoietic stem cells of the mouse", Nature, vol. 310, pp. 476–480 (1984).
Edwards, et al., "Alteration of morphogenesis by the v–myc oncogene in transplants of mammary gland", Oncogene, vol. 2, pp. 407–412 (1988).
Martin, "Isolation of a pluripotent cell line from early mouse embryos cultured in medium conditioned by teratocarcinoma stem cells", Proc. Natl Acad. Sci. vol. 78, pp. 7634–7638 (1981).
Evans, et al., "Establishment in culture of pluripotential cells from mouse embryos", Nature, vol. 292, pp. 154–156 (1981).
Doetschman, et al. Establishment of Hamster blastocyst–derived embryonic stem (ES) Cells, Developmental Biology, vol. 127, pp. 224–227 (1966).
Handyside, et al., "Cowards the isolation of embryonal stem cell lines from the sheep", Roux's Archives Dev. Biology, vol. 196, pp. 185–190 (1987).
Evans, "Origin of mouse embryonal carcinoma cells and the possibility of their direct isolation into tissue culture", J. Reprod. Fert., vol. 62, pp. 625–631 (1981).
Amoroso, "Placentation", Chapter 15, pp. 127–310.
Piedrahita, et al., "Isolation of Embryonic Stem cell–like colonies from porcine embryos", Theriogenology, vol. 29, No. 1, p. 296 (1988).
Martin, et al., "Differentiation of clonal lines of teratocarcinoma cells; Formation of Embryoid bodies in vitro", Proc. Natl. Acad. Sci., vol. 72, pp. 1441–1445 (1975).

*Primary Examiner*—Anne-Marie Baker
(74) *Attorney, Agent, or Firm*—Foley & Lardner

(57) ABSTRACT

A method of selecting and growing pluripotential embryonic stem cells isolated from an ungulate species blastocysts of embryos that develop by way of an embryonic disc is disclosed. The method comprises growing blastocysts in tissue culture growth medium which includes both heat-inactivated new born calf serum and heat-inactivated fetal calf serum; disaggregating the blastocysts either after spontaneous hatching or after mechanical removal of the zone pellucida; growing stem cell colonies from the disaggregated cells in issue culture growth medium; selecting stem cell colonies by morphological characteristics; and growing the selected stem cells in tissue culture growth medium. The cells are round cells, tightly packed with large nuclei in relation to cytoplasm, and fairly prominent nucleoli. They grow in tightly adherent coloedes and as the colonies get larger the cells tend to flatten out in the center of the colony. The outer, less flattened cells of a larger colony or all the cells of a smaller colony without central flattening are readily disaggregated by trypsinization into small spherical cells which have a bright phase contrast appearance, and if observed after a short time of incubation at 37° C. they show lobular pseudopodia.

2 Claims, 7 Drawing Sheets

US 6,436,701 B1

DERIVATION OF PLURIPOTENTIAL EMBRYONIC CELL LINES FROM UNGULATE SPECIES

BACKGROUND OF THE INVENTION

Mammalian Genetics

Traditional genetics depended upon mutations or pre-existing genetic polymorphisms which were discovered in a species. The only experimental approach to widen the scope of genetic variants available for study was mutagenesis followed by specific screening or fortuitous recovery of relevant alleles. Animal breeding depends upon selection from suitable variation either in or introduced into the stock. The major tool for genetic analysis was breeding segregation studies and direct phenotypic analysis.

Notwithstanding the great theoretical and practical interest in mammalian genetics the conventional genetic analysis of experimental mammals, because of their relatively small litter sizes and long life cycles, has been handicapped vis-a-vis other experimental animal systems. Mammalian genetics has, however, benefitted from the study of human genetics where although there is no experimental breeding, detailed observation of a very large population has allowed investigation both of polymorphisms and of very rare mutations, and statistical methods for analysis of data available from human pedigrees of genetic segregation have become highly refined.

Added to this, methods for non-meiotic genetic analysis—somatic cell genetics and more recently direct molecular-biological analysis, have been and indeed are being very effectively applied as well as being combined with pedigree analysis so that mammalian genetic maps and knowledge of gene sequence data are advancing rapidly.

This is, however, an observational analysis. Our understanding of genetic function and also, in experimental animals, the practical application of our genetic knowledge requires the ability deliberately to modify the genome, preferably in a manner not entirely reliant upon screening the accidents of nature. Thus the concept of a reverse mammalian genetics emerges where the effect of specific genetic modification may be studied in the context of the intact organism.

Genes of interest are now not only being identified from the results of the intensifying mammalian genetic analysis but importantly also through their molecular biology and by cross homology to those of other species. In a great number of cases there are genes which have been identified in mice through their molecular biology, by analogy with those of other species (e.g. human disease syndromes or Drosophila genetics) or from the biochemistry of their protein products but for which there is no lack-of-function allele and thus no rigorous genetic test of function. Neither are these mutations of protein structure or of genetic control. These can only be provided by creating such alleles. In the field of practical application to domestic farm animals, potential alteration of normal physiology which may be desirable, deletion or modification of function of controlling genes may be just as important as overexpression of others. The technology to undertake such targetted gene deletion or modification has now reached feasibility as exemplified by creation of null alleles at the hypoxanthine phosphorbosyl transferase gene—HPRT—locus [1] [2]. The development of methods which will allow targetting and screening for deletion of function or specific modification of any gene whose sequence is known is now well underway and this is clearly a realistic proposal. It will become an available routine technique for mouse cells in the next year or so and with the development of domestic animal embryonic stem cells will be immediately applicable to these species and may well become the transgenic route of choice.

Mammalian Transgenesis

Transgenic animals possess an alteration in their DNA which has been stably incorporated into the genome as a result of intentional experimental intervention. Typically this results from the additional exogenous foreign DNA or novel DNA constructs. With the advent of specific gene targetting we should not necessarily exclude from the definition of transgenesis specific modification of endogenous gene sequences by direct experimental manipulation.

A fully experimental approach to mammalian genetics is very rapidly becoming a reality through the use both of conventional zygote injection transgenics and of embryonic stem cells. The latter approach allows extensive in vitro genetic manipulation, selection and screening prior to whole animal reconstruction. Thus both an experimental molecular genetics and the ability to design genetic changes in animals are available. For practical purposes the mouse has been the species of choice for such studies but it is important to be able to extend the methods developed in the mouse to larger domestic farm animal species with the intention of their practical application. The new experimental mammalian genetics allows for testing of genetic modifications in vivo and designing genetic modification of a target species. One of the most important prospects is the construction of experimental animal models of disease for pharmaceutical testing and developments. The other is for specific modification of domestic farm animals to create more desirable qualities for food production, disease resistance, and biopharmaceutical protein production.

Methods for Transgenesis

Although DNA micro-injection is the most commonly used method of generating transgenic animals, alternatives include embryo infection using recombinant retroviral vectors incorporating the transgene and also the use of pluripotential embryonic stem (ES) cells.

In order to introduce genetic alterations into a mammal it is necessary to transform genetically a cell the progeny of which can give rise to all or to the desired part of the intact organism. zygote micro-injection [4] achieves transgenesis by transformation of the embryo's genome at the single cell or very early cleavage stage. As the germ line in mammals is segregated from somatic progenitor lineages at the early primitive-streak stage transformation of embryonic cells before this stage for instance by retroviral vector infection of cleavage embryos [5] may provide animals which are transgenic both somatically and in the germ line. Genetic transformation of cells after this stage will lead to either germ line or somatic genetic mosaicism. Where stem cells may be isolated from the organism these may be transformed and used to re-colonise their target tissue and the use of such techniques is exemplified by haematopoetic stem cell manipulation e.g. [7]. This type of approach to somatic transgenesis is likely to be the only ethical route for human gene therapy and could well prove particularly useful for genetic modification of domestic livestock and when the stem cells may be maintained in tissue culture prior to their use to reconstitute their target tissue there is the advantage that selection for the desired transformants may preceed reconstitution. See for example Edwards' use of transient culture of mammary epithelial stem cells [8]. Cells isolated from an embryo before segregation of the germ line are able to provide a genetic vehicle for germ line transgenesis. Whereas embryonic stem cells have been isolated from mice [9] [10] and cells which seem likely to have such properties from hamster, [11] it is by no means apparent that cells of a similar type may be necessarily isolated from other non-rodent embryos. Moreover it is unlikely that the methods as described for mouse and utilised for hamster will be directly applicable to other embryos. Indeed the reported failure (notwithstanding the optimistic title) of some competent researchers in the field [12] to isolate sheep embryonic stem cells by a method based upon that used for mouse embryonic stem cells indicates this. Others have isolated cells but failed to maintain lines or demonstrate their pluripotentiality [15]. Past failures may have been due to the expectation that the cells would be fast-growing and resemble those of the mouse. It was indeed reported that malignant transformation was necessary in order to overcome the inherent quiescence of the embryonic disc [6].

There have also been numerous attempts which have been orally reported at various scientific meetings which have been unsuccessful. When the mouse embryonic stem cells were first isolated virtually every expected property was predicted and the embryonic stage at which they might be found was clearly identified [13]. None of this background is available for putative ungulate embryonic stem cells.

We have discovered that the methods which have been established and described for the isolation of embryonic stem cells from mouse embryos and successfully applied to hamster embryos are NOT applicable to ungulate embryos as exemplified by bovine and porcine embryos. In particular the most important step in embryonic stem-cell isolation— identification and isolation of the stem cells from other cell types is quite differently based as is the necessary tissue-culture handling of the cells.

SUMMARY OF THE INVENTION

In accordance with the present invention, there is disclosed a method of selecting and growing pluripotential embryonic stem cells isolated from an ungulate species blastocysts of embryos that develop by way of an embryonic disc, comprising growing blastocysts in tissue culture growth medium which includes both heat-inactivated new born calf serum and heat-inactivated fetal calf serum; disaggregating the blastocysts either after spontaneous hatching or after mechanical removal of the zone pellucida; growing stem cell colonies from the disaggregated cells in tissue culture growth medium; selecting stem cell colonies by morphological characteristics; and growing the selected stem cells in tissue culture growth medium, wherein the morphologically selected cells are capable of culture in a tissue culture dish to exhibit the following morphological features:

a) they are round cells, tightly packed with large nuclei in relation to cytoplasm, and fairly prominent nucleoli;
  b) they grow in tightly adherent colonies, and as the colonies get larger the cells tend to flatten out in the center of the colony, with the colony having an outer rim of cells of the form described in a), and
  c) on trypsinization of such a colony it may be seen that the outer, less flattened cells of a larger colony or all the cells of a smaller colony without central flattening are readily disaggregated by trypsinization into small spherical cells which have a bright phase contrast appearance, and if observed after a short time of incubation at 37° C. show lobular pseudopodia.

BRIEF DESCRIPTION OF THE DRAWINGS

FIG. 4a is a photograph of a colony of cells derived from a seven-day blastocyst, showing large trophoblast-like cells, which are visible at the perimeter. FIGS. 4b and 4c are photographs of stem-like cells, which are epithelial, adherent and have large nuclei and prominent nucleoli, the cultures are derived from seven-day and eight-day blastocysts, respectively.

FIG. 5a is a photograph of a nest of undifferentiated cells. FIG. 5b is a photograph of a confluent monolayer of cells. FIG. 5c is a photograph of a confluent monolayer showing morphological differentiation into neuron-like cells.

FIGS. 6b to 6d are photographs of outgrowths of cells from aggregates which were permitted to reattach to a substratum, showing (b) epithelial, (c) muscle and fibroblastic and (d) nerve-like cells, respectively.

DETAILED DESCRIPTION OF PREFERRED EMBODIMENTS

Figure 1:
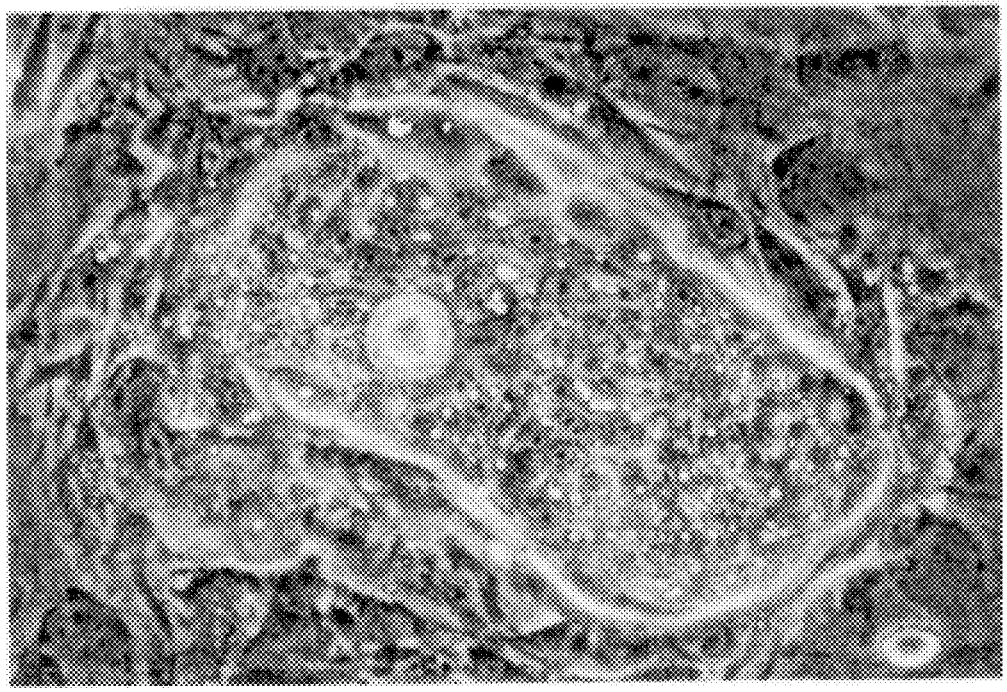
FIG. 1 is a photograph of colonies of stem cells growing in cell culture.

Early Mammalian Development: Theoretical Consideration for the Isolation of Stem Cells from Ungulates In mammals, the pattern of embryonic development from fertilisation to implantation is broadly similar between species: fertilisation of the oocyte occurs in the oviduct, and the zygote is transported to the uterus whilst undergoing a series of mitotic divisions. At each division cell size decreases, and so the volume of the embryo reman constant. A blastocyst is formed at a certain stage, when a cavity appears within the embryo. At this time the cells have differentiated into two types, the trophoblast and the inner cell mass, destined to become the fetal portion of the placenta and the fetus, respectively. However, by the time of implantation great differences are observed between species. In particular in the mouse, implantation into the uterine epithelium is an invasive and rapid process (14). In ungulates, in particular in cattle, sheep and pigs, implantation occurs only after a considerable delay during which the trophectoderm proliferates rapidly and the inner cell mass forms a quiescent embryonic disc. In these cases implantation involves loose association between the fetal cells and the maternal cotyledons (14). Thus early development at the time when stem cells may be isolated is very significantly different in many species including ungulates from the mouse.

Procedures for the isolation of murine embryonic stem cell lines are now well established. Success in the isolation of embryonic stem cells from the mouse depended on the recognition of the need for careful timing, so that ICM cells are committed to the ICM lineage and yet are free from the influence of differentiated derivatives [9]. Although, by extrapolation, it can be argued that stem cells may be isolated similarly from the ungulates and other. species, we anticipated that problems would arise in that exactly analogous stages do not exist in the embryos of mice and ungulates owing to difference in their development. We inferred that a different strategy will be required for the ungulates as, for example, the rate of development is much slower and the early embryonic ectoderm is present in a discoid arrangement and not as a solid mass as in the 5 day mouse embryo. These considerations led us to predict that the embryonic cells of the pre-implanting embryo, owing to the obligatory period of metabolic quiescence of the embryonic disc, would not be culturable with facility in vitro; and that stem cells, if isolated, would not necessarily resemble mouse embryonic stem cells in morphology or growth characteristics. In these situations recognition of the stem cell types would be difficult. Nevertheless, we are able to define those conditions which are sufficient for the isolation of stem cells from ungulates, and for preventing cell differentiation sufficiently for cell lines to be established. It is likely that the cell type required and the means of its isolation may prove more general than that of embryonic stem cell isolation in the mouse as many other mammalian embryos—for example primate embryos—develop through an embryonic disc more similar to the structure found in ungulates than the epiblast and egg cylinder seen in the mouse and some other rodents.

Method of Isolation and Culture of Embryonic Stem Cells from Ungulate Eryos

1. Tissue Culture Medium

Dulbecco's modified DMEN culture medium supplimented with 5 to 10 percent of both foetal and new born calf serum, non-essential amino acids to the Eagles formula and 0.1 Millimolar 2-mercaptoethanol is used. Particular attention to selection of the sera is essential and unlike most sera used for mouse embryonic stem cell derivation, it was found that heat-inactivation of the serum at 56 degrees centigrade for 30 minutes was necessary.

2. Explantation of the Embryo

Both species of embryo behave differently in culture from the mouse. In the case of the bovine embryos the procedure is as follows:

Either fresh 6 day embryos flushed from in vivo or preferably embryos which have been grown in vitro from in vitro fertilised in vitro matured oocytes (supplied by Animal Biotechnology Cambridge Ltd.) at 6–7 days of development—unhatched, fully expanded blastocysts—are grown from 1 or two extra days in tissue culture medium. They either hatch spontaneously or are freed from their zona pellucida mechanically and allowed to explant upon the bottom of a petri dish containing an STO fibroblast feeder layer as previously described [9]. Unlike the case with a muse embryo the inner-cell-mass derived cells do not form a central egg cylinder. Their derivatives which may be isolated as the precursors of the embryonic stem cells are found on the periphery of the explant. These are isolated by careful trypsinisation using trypsin/EGTA/polyvinyl alcohol (0.25%:0.1 mM:10 ug/ml respectively) and replated as below.

For porcine embryos the procedure is: Embryos from the stage of hatching (6.5 days) to trophoblast expansion (11 days) are either explanted intact in which case most of the trophoblast layer dies, or preferably dissected to isolate the embryonic disc before this is explanted onto a fibroblast feeder layer typically inactivated STO fibroblasts. Primary outgrowths may be recognised to be the precursors of the embryonic stem cells and these are disaggregated and passaged. These primary stem cell outgrowths are different from the established cell lines and appear as more translucent and flatter tightly-packed epithelial colonies.

3. Feeder Cells and Growth Factors

It is sufficient to use STO fibroblasts as feeder cells for either species. It is not necessary to use exogenous growth factors or conditioned media.

4. Recognition and Isolation of the Stem Cells

Unlike those of the mouse and hamster, the ungulate embryonic stem cells do not form multilayered colonies but grow in distinctive flat polarised epithelial colonies which eventually spread to form monolayer. The cells are larger than those of the mouse, have large clear nuclei, several prominent nucleoli and relatively little cytoplasm. The cell size is found to vary from isolation to isolation and with growth conditions but the general morphology and appearance is distinctive.

Other non-epithelial cell types may be observed and isolated but these do not have the differentiative properties described.

5. Maintenance of Cells in Culture

Cells are passaged 1 in 4–5 by trypsinisation onto fresh feeder cells at 3–4 day intervals or just before they attain confluency. Failure to passage prior to confluency results in the onset of spontaneous differentiation which if allowed to continue leads to loss of the cell line. Undifferentiated colonies may be able to be recovered after partial differentiation of the culture. The cells will grow without feeders but their ability to form embryoid bodies becomes compromised.

6. Verification of the Stem Cells

Figure 7A:
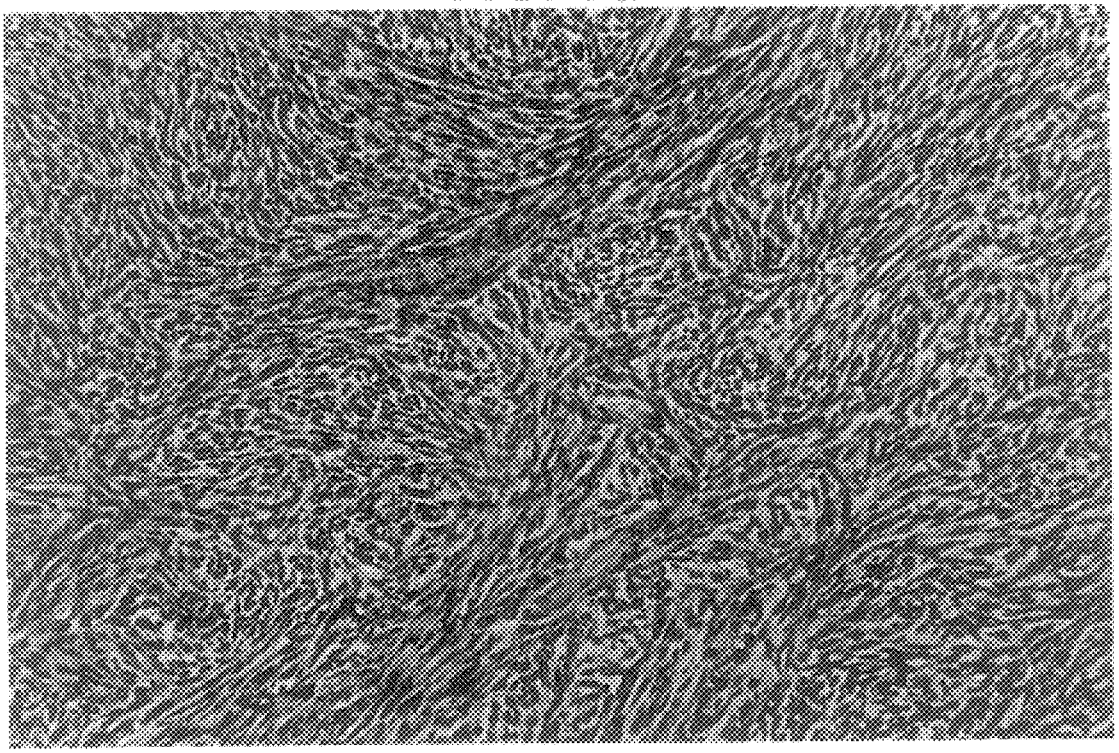
FIGS. 7a and 7b are photographs of teratocarcinomas showing a variety of differentiated cell types.
Figure 7B:
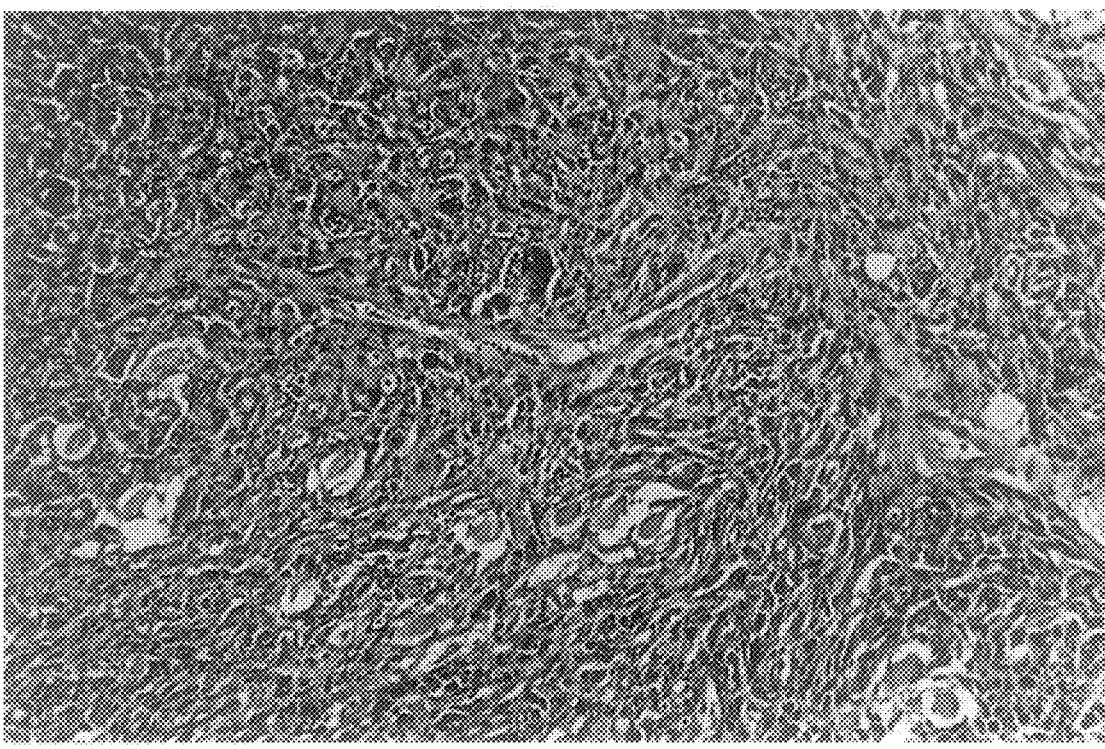

These cells differentiate readily in culture either spontaneously or in response to morphogens such as dimethyl sulphoxide or retinoic acid. The main differentiated derivatives are fibroblast, nerve endoderm and muscle which are representative of the three germ layers and verities the pluripotentiality of the cells. Moreover these cells will form tunours when transplanted beneath the kidney capsule of an irradiated nude mouse, these tumours being teratocarcinomas showing a variety of differentiated cell types (FIGS. 7a and 7b).

On aggregation in vitro embryoid bodies are formed. These are distinctly different from those of the mouse by virtue of the fact that they show a polarisation akin to that seen in those formed by human teratocarcinona cells. Explanation of these embryoid bodies into a tissue culture dish results in rapid and extensive differentiation.

All these observations demonstrate that the cultures described are indeed embryonic stem cells.

The present invention can provide stem cells, and a general method as exemplified above for isolation of embryonic stem cells from all embryos. in which development is via an embryonic disc in particular ungulate embryos (such as porcine embryos and bovine embryos). The invention can provide for the derivation of such cells from embryos carrying a particular genetic background or specific mutations. For example derivation of such cells from high-pedigree agricultural stock. It can also provide a method for preparation and use of such cells for differentiation and developmental studies in vitro, together with a method of use of such cells as a source of any other differentiated cell in vitro or in vivo. Furthermore, the invention can provide for the use of such cells to repopulate an embryo of the same species thus giving rise to a chimaeric animal, particularly a chimaeric animal in which some or all of the germ cells are derived from the tissue-culture cells; for example a chimaeric animal in which some or all of the germ cells are derived from the tissue-culture cells where the embryonic stem cells have been genetically modified or selected for genetic modification in culture. Stem cells according to the invention can be cultured either transiently or maintained as a cell line to provide nuclei for nuclear transfer into enucleated oocytes or other embryonic cells, e.g. using cells with specific genetic properties either by virtue of their provenance from specific embryos or otherwise by specific genetic modification.

The invention can allow development of embryos from cells which have received a necleus from an embryonic stem cell cultured in vitro. It can allow the use of stem cells genetically transformed in such a way as to introduce a novel protein production in a specific part (e.g. the mammary gland, the liver) of a subsequently derived chixraeric animal or the offspring of such a chimaeric animal, or a subsequently derived nuclear-cloned animal or the offspring of such an animal to provide nuclei for neclear transfer into enucleated oocytes or other embryonic cells.

Stem cells of the invention may be used in techniques of genetic transformation and may be used in the creation of embryos to produce a genetically transformed living animal by embryo transfer. enabling modification of the resulting animals and enabling production of an animal having desired characteristics.

In a further aspect the present invention provides a method of obtaining bovine stem cells, comprising growing bovine blastocysts in tissue culture growth medium; causing disaggregation of the blastocysts after hatching; growing the disaggregated cells in tissue culture growth medium; selecting stem cell colonies by morphological characteristics; and growing the selected stem cells in tissue culture growth medium.

The invention also provides a blastocyst to which has been introduced one or more bovine stem cells of the invention, and the chimaeric progeny of such a blastocyst.

The invention will be further described, by way of illustration, in the following example and with reference to the accompanying figures.

FIG. 1 is a photograph of colonies of stem cells growing in cell culture; and

Figure 2:
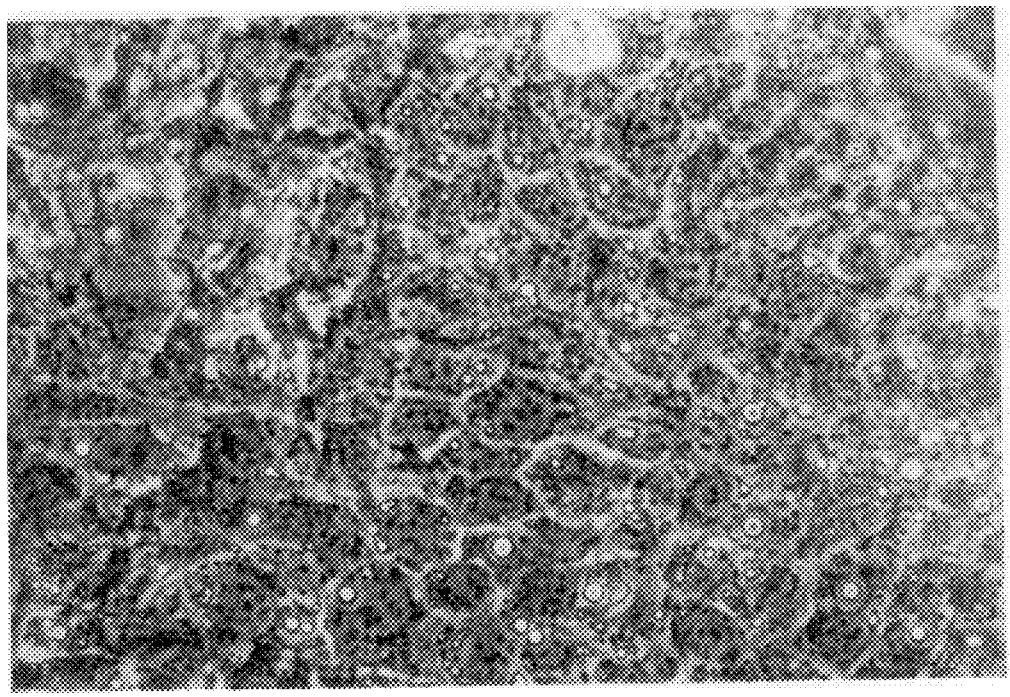
FIG. 2 is a photograph of a monolayer of bovine stem cells.

FIG. 2 is a photograph of a monolayer of bovine stem cells.

EXAMPLE

Bovine embryos are treated by the following procedure:

The embryos may be fertilised in vivo, in which case they are obtained by flushing from a cow by known techniques at 5–6 days embryonic development. However, it is preferred to use embryos fertilised in vitro and the following work was carried out using fresh expanded bovine blastocysts derived by in vitro fertilisation and obtained from Animal Biotechnology Cambridge Limited, Cambridge, England. Similar material may also be obtained from other commercial sources. The blastocysts may also be obtained in frozen form, but it is preferred to use fresh blastocysts.

The blastocysts are grown on a culture dish, in tissue culture growth medium on a feeder layer of mytmycin inactivated STO cells. The medium used consists of a mixture of 75 parts of Dulbecco's Modified Eagles medium (MEM) to 25 parts of Ham's F12M Medium, supplemented with non essential amino acis (Eagle's) (about 1% by volume), beta mercapto ethanol to $10^{-4}$ molar, 50 units/ml penicillin G, 10% new born calf serum and 10% foetal calf serum, both sera having been heat inactivated at 56° C. for 30 minutes before use. The blastocysts are incubated at 37° C. in a carbon dioxide gas humidified incubator in an atmosphere of about 5% carbon dioxide in air.

The incubating blostocysts are periodically examined using a microscope, say twice daily, until hatching is observed. The timing of this varies with different embryos, but will typically be after about 2 days.

The hatched blastocysts are then treated in one of two alternative ways.

1) In a first approach, about 1 day after hatching the blastocysts are treated by being soaked for about 10 minutes in trypsin (0.25% Difco trypsin 1 in 250) supplemented with $10^{-4}$ molar EGTA (ethylene glycol tetracetic acid) and 10 ug/ml The scope of this invention extends to cover not only the stem cells per se, but to embryos and genetically transformed animals derived therefrom. The invention also covers essentially non-biological methods for production of stem cells, embryos and animals.

According to one aspect of the invention there is provided a bovine stem cell line; and a method for its production.

This aspect of the invention also provides a cell culture system comprising bovine stem cells.

Bovine stem cells are conveniently produced by growing bovine blastocysts (fertilised in vivo or in vitro) in suitable tissue culture growth medium. One preferred medium consists of a mixture of 75 parts of Dulbecco Modified Eagles Medium (DMEM) to 25 parts of Ham's F12M Medium, supplemented with non essential amino acids (Eagle's) (about 1% by volume), beta mercapto ethanol $10^{-4}$M, 10% new born calf serum and 10% foetal calf serum, both sera having been heat inactivated by treatment at 56° C. for 30 minutes before use.

After hatching the blastocysts are desirably treated to cause disaggregation. This is preferably effected by treating the blastocysts about 1 day after hatching by soaking for about 10 minutes in trypsin (0.25% Difco trypsin 1 in 250) supplemented with $10^{-4}$ molar EGTA (ethylene glycol tetracetic acid) and 10 ug/ml polyvinyl alcohol, followed by physical treatment to cause disaggregation, e.g. by sucking and blowing through a small pipette.

Hence in a preferred aspect the present invention provides a method of obtaining bovine stem cells, involving the steps of growing bovine blastocysts in tissue culture growth medium, and soaking the blastocysts about 1 day after hatching for about 10 minutes in trypsin supplemented with EGTA and polyvinyl alcohol to cause disaggregation of the blastocysts.

After disaggregation, the disrupted blastocyst cells may be replated and grown in a further supply of the growth medium together with inactivated STO cells, resulting in the growing up of colonies of cells of at least 2 different types.

After a suitable incubation line colonies of stem cells can be selected by morphology, as described below. The cells are grown up in the growth medium plus inactivated SMO cells, with the cells passaged about once a week.

After the 4 th or 5 th passage then cells can be subjected to further treatment of different types.

For example, the cells can be frozen if required for storage.

Alternatively the fresh cells can be introduced to a host blastocyst e.g. using conventional micromanipulation techniques. Typically between 1 and 15 cells are introduced to a host blastocyst. The blastocyst can then be introduced to the uterus of a pseudopregnant foster mother where it may develop into a chimaeric animal.

Prior to introduction to a host blastocyst, the cells can if desired by manipulated in culture by known techniques, e.g.

by DNA transformation, targetted rotation by homologous recombination, or infection with retroviral vectors, so polyvinyl alcohol. This mixture acts to disaggregate the cells of the blastocysts while maintaining cell viability.

Using a small pipette, with a tip about 50 to 100 microns in diameter the cells are then physically disaggregated by sucking and blowing, causing the cells to fall into clusters, breaking down the blastocyst structure.

The disrupted blastocyst is immediately subjected to further treatment, described below.

2) In an alternative approach the hatched blastocysts are left in the tissue culture medium and allowed to develop further. After about 3–4 days development it is observed that the inner cell mass of the blastocyst is found in clusters of rounded cells located around the edge of the explant. At this stage the trypsin mixture used in 1) above is added to the culture dish and left for about 10 minutes. It is found that the cell clusters at the edge of the explant loosen more easily than others, and these cells are picked off using a small pipette with a tip about 20 to 30 microns in diameter, and transferred for further treatment.

After treatment by method 1) or 2) the disrupted blastocyst cells are replated into a tissue culture dish surface treated with a gelatin solution. A further supply of the growth medium described above is added, together with about $10^{-6}$ inactivated STO cells, and the dish placed in an incubator at 37° C.

The cells are periodically examined by microscope, e.g. daily. Colonies of cells of at least 2 different types are observed growing up.

After a suitable incubation time colonies believed to be stem cells are selected by morphology: stem cells have the following features:

a) They are round cells, tightly packed with large nuclei in relation to cytoplasm, and fairly prominent nucleoli.

b) They grow in tightly adherent colonies. As the colonies get larger the cells tend to flatten out in the center of the colony, with the colony having an outer rim of cells of the form described in a).

c) On trypsinisation of such a colony using the trypsin mixture described in 1) above it may be seen that the outer, less flattened cells of a larger colony or all the cells of a smaller colony without central flattening are radily disaggregated into small spherical cells which have a bright phase contrast appearance, and if observed after a short time of incubation at 37° C. show lobular pseudopodia.

Such colonies are illustrated in FIG. 1.

Suitable colonies, believed to be of stem cells, are selected and transferred to another dish, to which is added a further supply of the growth medium together with inactivated STO cells. The dish is placed is an incubator at 37° C. to allow colonies of the cells to grow up.

The cells are passaged about once a week, i.e. subjected to the trypsin treatment as described in 1) above and replated onto a new dish. This is to stop differentiation.

If the cells are to be stored they are frozen after the 4 th or 5 th passage.

Otherwise, cells at this stage can be introduced to another, host, bovine blastocyst: typically between 1 and 15 cells are introduced to a blastocyst using conventional micromanipulation techniques. The blastocyst can then be introduced to the uterus of the pseudopregnant foster mother in known manner, or maintained in an artificial environment, in the uterus develop into a chimaeric animal containing DNA from both the host blastocyst and the introduced cells. Chimaerism can be detected in known ways, e.g. by use of genetic markers, or possibly simply by visual inspection.

Prior to introduction to a host blastocyst, the cells can be manipulated in culture by known techniques, e.g. by DNA transformation or infection with retroviral vectors, so enabling modification of the resulting animals and enabling production of an animal having desired characteristics.

According to another aspect of the invention there is provided a porcine stem cell line, and a method for its production. This aspect of the invention also provides a cell culture system comprising porcine stem cells.

Figure 3:
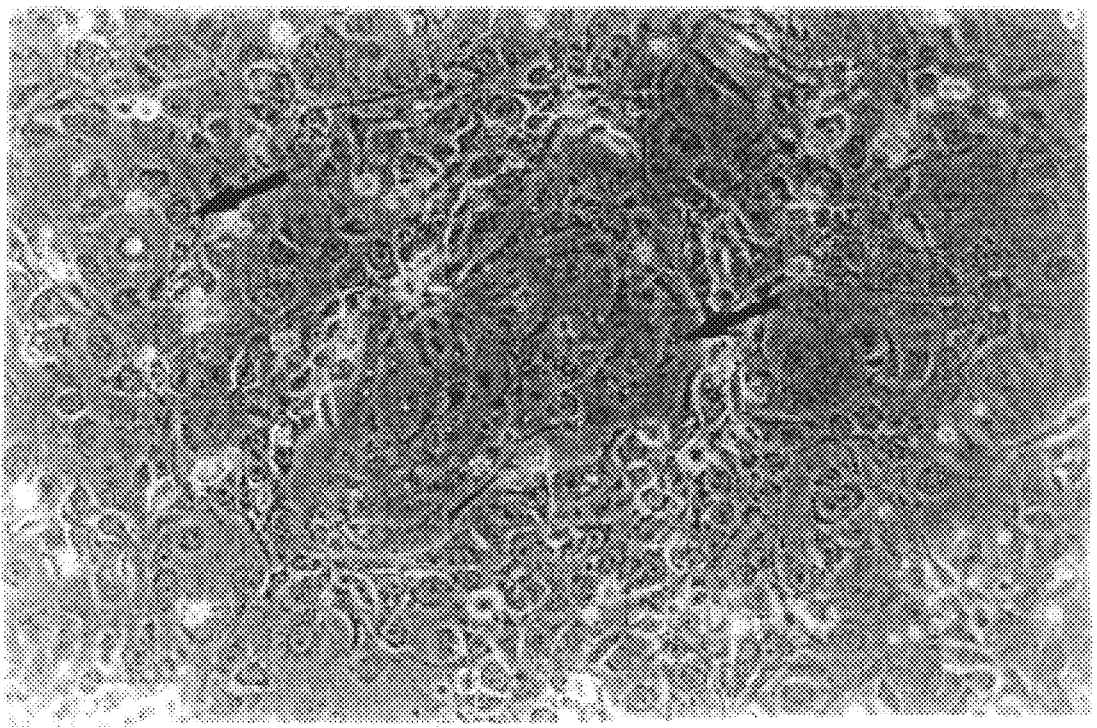
FIG. 3 is a photograph showing the appearance of a primary colony resulting from the attachment of the inner cell mass from an eight-day blastocyst.
Figure 4A:
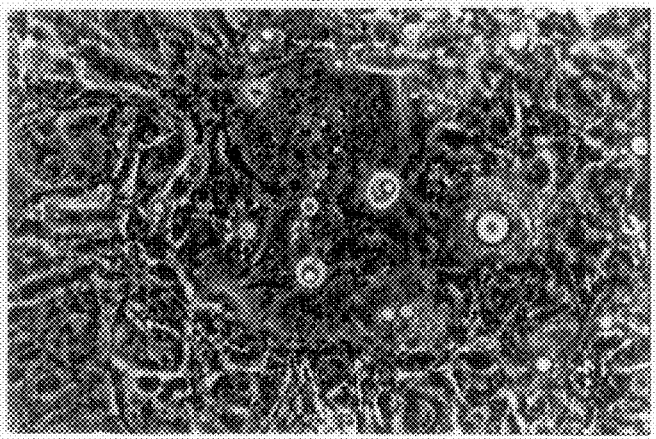
FIGS. 4a–c shows morphologies of colonies resulting from disaggregated primary outgrowths of inner cell masses.
Figure 4B:
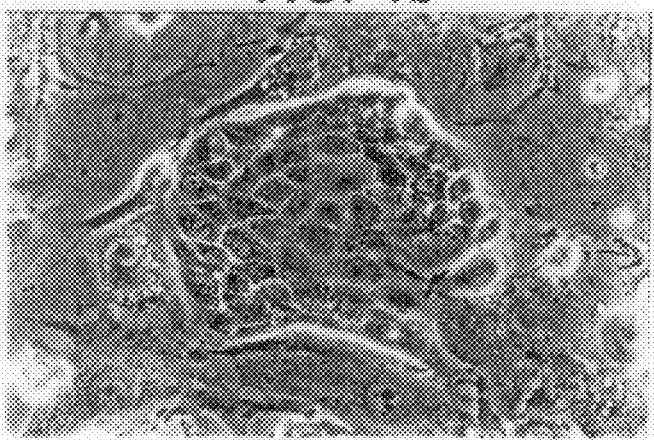

This aspect of the invention will now be further described, by way of illustration in the following example and with reference to the accompanying figures in which are:

FIG. 3. Appearance of primary colony resulting from attachment of inner cell mass from 8d blastocyst. The flattened, translucent colonies are arrowed: Morphologies of colonies resulting from disaggregated primary outgrowths of inner cell masses. FIG. 4a; colony of cells producing large, trophoblast-like cells, which are visible at the perimeter. This culture was derived from a 7d blastocyst. FIGS. 4b; and 4c; colonies of stem-like cells, which are epithelial, adherent and have large nuclei and prominent nucleoli. The colony shown in FIG. 4b derived from a 7d blastocyst, and that in 4 c from an 8 d blasocyst.

Figure 5A:
FIGS. 5a–c shows morphological differentiation in an established porcine cell line.
Figure 5B:
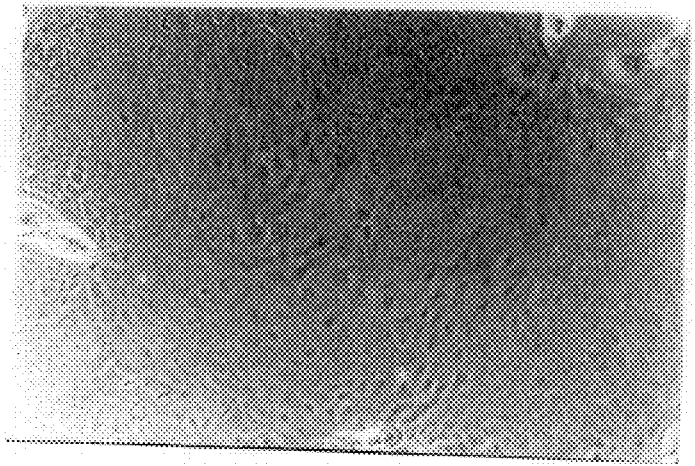
Figure 5C:

FIG. 5. Established porcine cell line showing morphological differentiation. FIG. 5a. Nest of undifferentiated cells. FIG. 5b. Confluent monolayer of cells. FIG. 5c. Confluent monolayer showing morphological differentiation into neuron-like cells.

Figure 6A:
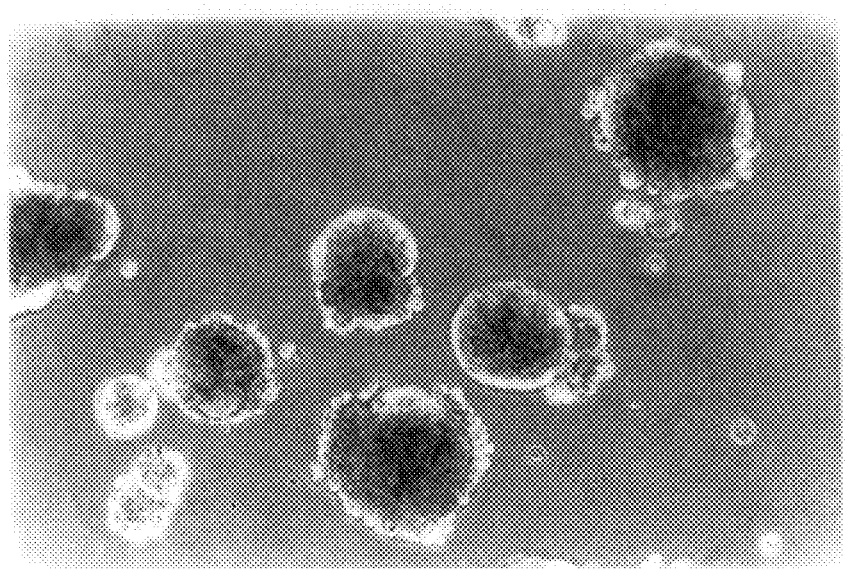
FIGS. 6a–d is a photograph of aggregates formed by a porcine cell line following culture for 7 days on a non-adhesive substratum.

FIG. 6a. Aggregates formed by porcine cell line following culture for 7d on a non-adhesive substratum.

Figure 6B:
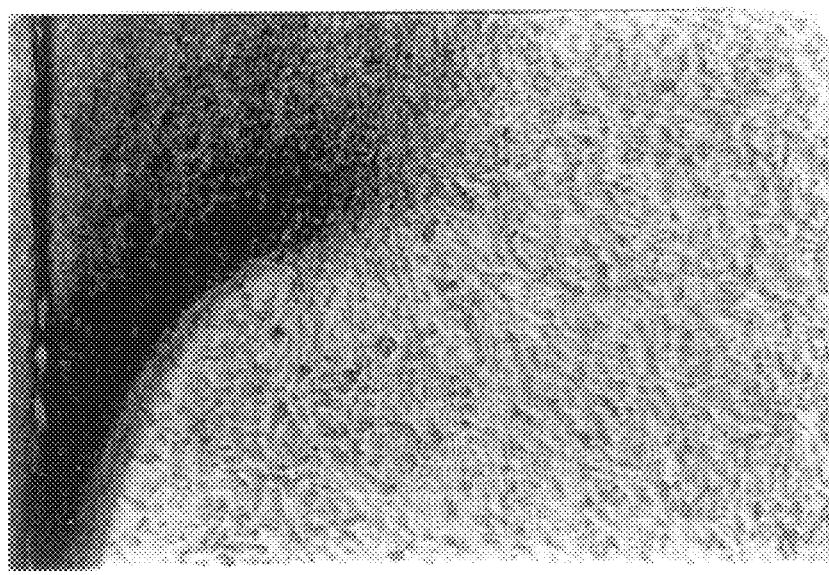
Figure 6C:
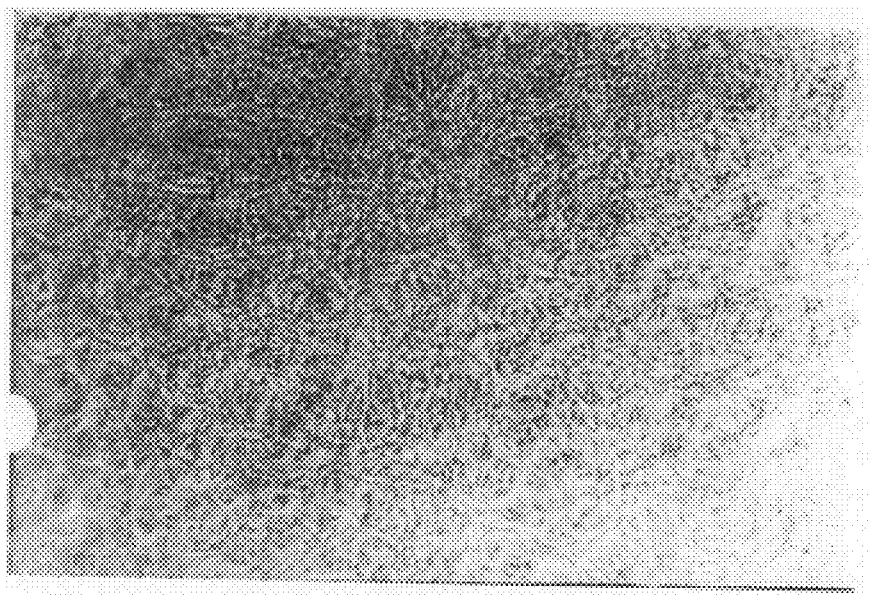
Figure 6D:

FIGS. 6b to 6d. Outgrowths of cells from aggregates which were permitted to reattach to a substratum. Several differentiated cell types are visible; 6b epithelial, 6c muscle and fibroblastic and 6d nerve-like.

Hatched blastocysts were recovered by retrograde uterine flushing from Large British White gilts at 7–9 days post oestrus. The animals were naturally mated and not superovulated. Either intact blastocysts or the inner cell masses manually dissected from them were explanted onto STO fibroblast mitotically-inactivated feeder cells in a manner similar to that described by Evans & Kaufman (1981) [9] for muse blastocysts. The medium used was Ducco's modified Eagle's medium supplemented with 10% new born calf serum and 5% to 10% foetal calf serum, and 0.1 mllimolar 2-mercaptoethanol, and neither conditioned medium nor exogenous growth factors were added.

In order to stimulate organised differentiation, cells were disaggregated by trypsinisation and then seeded onto culture dishes which had been coated with a layer of 0.5% agarose as described by Magrane (1982) [3] for stimulation of formations of embryoid bodies by human teratocarcinom cell cultures. To enhance cell differentiation both mercaptoethanol and foetal calf serum were omitted from the medium.

Establishment of Cultures

We have by these methods of cultures been able routinely to establish cultures from explanted porcine embryos. Although the success rate is variable it is often high with as many as 6 successful cultures being derived from 8 explanted blastocysts in one experiment.

When blastocysts or embryonic discs are brought into culture, they attach within one day. The primary outgrowths consist of colonies of large flat, highly-translucent epithelial cells (FIG. 3). These are clearly of very different appearance and culture rorphology to murine EK cells. Portions of trophectoderm dissected from blastocysts between the ages of 7–10 days and cultured in the same way were unable to form colonies or outgrowths.

The primary outgrowths were dissaggregated 7–14 days after explantation and passaged to fresh feeder layers. Pregressively growing colonies were formed which grew as a monolayer with very distinct colony boundaries. The cells are epitheolioid with large clear nuclei containing 2–4 prominent nucleoli, and relatively sparse cytoplasm. Sore differences in the appearance of these cells have been noticed between different isolates which is principally related to cell size.

FIG. 4 shows small colonies of large, undifferentiated cells which continuously produce cells with morphological characteristics of trophoblast giant cells. Such cultures have been maintained for 4 months in continuous culture. Cultures of this type have only been observed to arise from 7 day embryos.

FIG. 4b shows a cell type which is more stable and able to grow in larger colonies. These cells are the most common isolate. Several cell lines of the type shown in FIG. 4b have been derived from both 7 and 9 day embryos. One cell line has been maintained in continuous culture for more than one year with passaging 1 in 4 every 5–7 days without change of cell phenotype. It therefore appears to be immortal differentiation of these cells occurs spontaneously when the cells are permitted to reach high density (FIG. 5). Overtly differentiated cells fail to reattach on passage leading to regeneration of undifferentiated cultures.

Figure 4C:
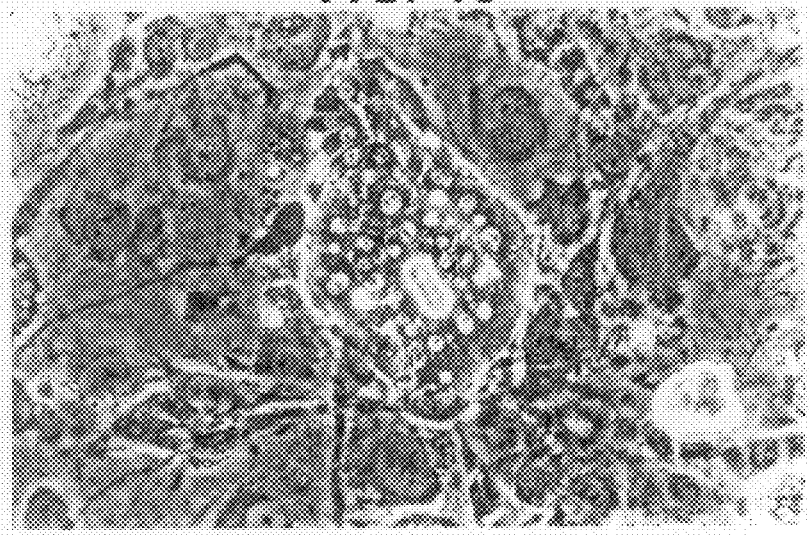

FIG. 4c shows a colony of smaller cells which are a more rarely isolated form.

All of these cell types grow more slowly than and differ in appearance to mouse embryonic stem cells. They show spontaneous differentiation in culture mainly into trophoblast-like cells or endoderm-like cells. Other differentiated (mainly fibroblastoid) cell types are also formed.

Differentiation into Embryoid Bodies

As a test of differentiation potential (Martin & Evans 1975) [16] cells from the cell line which had been maintained for 12 months were induced to form aggregates by seeding onto a non-adhesive substratum. After several days an outer smooth layer of cuboidal epithelial cells appeared at one end of the aggregates and at the other pole there were more loosely attached cells of a more raged appearance. Extensive differentiation occurred when the embryoid bodies were permitted to attach to the substratum, by replating onto tissue-culture dishes (FIG. 6b). Cells migrated and multiplied to form dense cultures, with several types visible, including epithelium, endoderm, muscle and neural cells. These differentiated cells are representative derivatives of all three embryonic germ layers, and suggest that the stem-cell-like culture represents a primary ectodermal lineage of the pre-somite embryo.

Discussion

The cell lines isolated have an appearance considerably different although slightly reminiscent of marine embryonic stem cells. In appearance and form of growth they are more similar to some cell lines derived from human testicular teratocarcinomas. The form of development of their aggregates when maintained in suspension is very similar to that of a human teratocarcinoma cell line Hutt M (as described in Magrane 1982) [3]. We tentatively conclude that these differentiating structures are indeed homologous to the murine embryoid bodies and this conclusion is strengthened by the observations reported here of a more extensive in vitro differentiation following their re-explanation onto a tissued-culture surface. One of us (MJE) has previously speculated that the assymetric form of the Hutt KEB embryoid bodies reflects the development of the human embryo via an embryonic disc in contrast to the mouse egg cylinder. It is interesting to note here that in another species where early development is via an embryonic disc with a clearly epithelioid embryonic epiblast, the isolated cells grow more as a monolayer than in the piling colonies typical of mouse EC and EK cells and differentiation of their erbryoid bodies is clearly assymetric. This distinctly different behaviour from that of mouse EK cells may be a general feature of those non-rodent embryos where embryonic development is via an embryonic disc.

We conclude that pluripotent embryonic lineages may be derived from the pig and can be maintained in culture.

These are very different both in appearance, growth characteristics and behaviour to those previously described in the mouse. The clear similarity between porcine cell lines and those seen from bovine embryos strongly supports the suggestion that this type of embryonic cell lineage is the form of cell line which will be obtained from mammalian species in general developing via an embryonic disc, examples of such species being e.g. ungulates. We are currently evaluating the potential of our embryonic cells, to determine (a) their relationship to normal embryonic cells, and to determine their distinctive features compared to the murine EK lineages, and (b) whether there exist restricted potency stem cell populations which may be transitory in nature, and (c) the origin and nature of those cells which are capable of expressing pluripotency under certain conditions. It is notable that the rate of proliferation of undifferentiated, stem-like cells in explants of porcine embryos is slower compared with those derived from murine embryos. This may reflect another important difference in pre-inplantational development in these species, that is the period of quiescence of the inner cell mass in ungulates up to the time of gastrulation.

As these new cell lines may be considered homologous to murine EK cells they have the potential as a vector for genetic manipulation by their incorporation into a normal fertile pig via embryo chimaerism leading to their contribution to the germ cell line.

References

[1] M R Kuehn, A Bradley, E J Robertson and M J Evans.
A potential animal model for Lesch-Nyhan syndrome through introduction of HPRT rotations into mice.
NATURE 326 295 (1987)

[2] M L Hooper, K Hardy, A Handyside, S Hunter and M Monk.
HPRT-deficient (Lesch-Nyhan) mouse embryos derived from germline colonisation by cultured cells.
NATURE 326 292 (1987)

[3] Magrane G. G. (1982)
A comparative study of Human and Mouse Teratocarcinomas. PhD Thesis University of London.

[4] Palmiter R D & Brinster R L
Germline transformation of mice.
ANN.REV. GENETICS 20 465 (1986)

[5] Van der Putten H., Botteri F. M., Miller A. D., Rosenfield M. D., Fan H., Evans R. M. & Verma I. M.
Efficient insertion of genes into the mouse germ line via retroviral vectors.
Proc Natl Acad Sci 82 6148–6152 (1985)

[6] Mcihir J.
Ph.D. thesis "Embryonic cell lines in farm animals".
University of Calgary (1989)

[7] Williams D. A., Leshka I. R., Nathan D. G. & Mulligan R. C.
Introduction of new genetic material into pluripotential haematopoetic stem cells of the mouse.
NATURE 310 476–480 (1984)

[8] Edwards P. A. W., Ward J. L. & Bradbury J. M.
Alteration of imrphogenesis by the v-myc oncogene in transplants of mammary gland.
Oncogene 2 407–412 (1988)

[9] Evans M J & Kaufman M H
Establishment in culture of pluripotential cells from mouse embryos.
NATURE 292 154–156 (1981)

[10] Martin G. R.
Isolation of a pluripotent cell line from early mouse embryos cultured in medium conditioned by teratocarcinom stem cells.
Poc Natl Acad Sci 78 7634–7638 (1981)

[11] Doetschman T., Williams P. & Maeda N.
Establishment of hamster blastocyst-derived embryonic stem (ES) cells.
Dev. Biol 127 224–227 (1988)

[12] Handyside A., Hooper M. L., Kaufman M. H. & Wilhut I.
Towards the isolation of stecell lines from the sheep.
Roux archive of developmental biology 196 185–190 (1987)

[13] Evans M.
Origin of mouse embryonal carcinoma cells and the possibility of their direct isolation into tissue culture.
J. Reprod. Fert. 62 625–631 (1981)

[14] Am1 roso E. C.
Placentation. In "Marshall's Physiology of Reproduction", 3 rd edn., Vol. 2.
pp 127–311. Ed. A. S. Parkes, Longnans, Green & Co., London.

[15] Piedrahita J. A., Anderson G. B., Martin G. R.,
Bon Durant R. H. Pashen R. L.
Theriogenology 29 286 (1988).

[16] Mrtin G. R. & Evans M. J. (1975)
Differentiation of clonal lines of teratocarcinama cells: formation of embryoid bodies in vitro.
Proc. Natl. Acad. Sci. USA 72, 1441–1445.

What is claimed is:

1. A method of selecting and growing pluripotential embryonic stem cells isolated from an ungulate species blastocysts of embryos that develop by way of an embryonic disc, comprising the steps of:

growing blastocysts in tissue culture growth medium which includes both heat-inactivated new born calf serum and heat-inactivated fetal calf serum;

disaggregating the blastocysts either after spontaneous hatching or after mechanical removal of the zone pellucida;

growing stem cell colonies from the disaggregated cells in tissue culture growth medium;

selecting stem cell colonies by morphological characteristics; and growing the selected stem cells in tissue culture growth medium;

wherein the morphologically selected cells are capable of culture in a tissue culture dish to exhibit the following morphological features:

a) they are round cells, tightly packed with large nuclei in relation to cytoplasm, and fairly prominent nucleoli;

b) they grow in tightly adherent colonies, and as the colonies get larger the cells tend to flatten out in the center of the colony, with the colony having an outer rim of cells of the form described in a), and c) on trypsinization of such a colony it may be seen that the outer, less flattened cells of a larger colony or all the cells of a smaller colony without central flattening are readily disaggregated by trypsinization into small spherical cells which have a bright phase contrast appearance, and if observed after a short time of incubation at 37° C. show lobular pseudopodia.

2. A method according to claim 1, further including passaging the selected stem cells by trypsinisation onto fresh tissue culture growth medium at intervals to prevent differentiation of the cells and to maintain a cell line in culture.

* * * * *